United States Patent
Nishimura

(10) Patent No.: US 7,304,176 B2
(45) Date of Patent: Dec. 4, 2007

(54) PROCESS FOR PRODUCING EASILY POLYMERIZABLE SUBSTANCE

(75) Inventor: Takeshi Nishimura, Hyogo (JP)

(73) Assignee: Nippon Shokubai Co., Ltd., Osaka (JP)

(*) Notice: Subject to any disclaimer, the term of this patent is extended or adjusted under 35 U.S.C. 154(b) by 96 days.

(21) Appl. No.: 10/844,313

(22) Filed: May 13, 2004

(65) Prior Publication Data

US 2004/0242826 A1 Dec. 2, 2004

(30) Foreign Application Priority Data

May 14, 2003 (JP) .............................. 2003-136374

(51) Int. Cl.
*C07C 51/44* (2006.01)
(52) U.S. Cl. ...................... 560/218; 562/546; 562/598; 562/600; 203/3; 203/8; 203/38; 203/59
(58) Field of Classification Search ................ 560/218; 562/598, 546, 600; 203/3, 8, 38, 59
See application file for complete search history.

(56) References Cited

U.S. PATENT DOCUMENTS

| 4,873,368 A |   | 10/1989 | Kadowaki et al. |
|---|---|---|---|
| 5,360,926 A | * | 11/1994 | Kouno et al. ................ 560/205 |
| 5,651,927 A | * | 7/1997 | Auda et al. .................... 264/85 |
| 5,785,821 A |   | 7/1998 | Sakamoto et al. |
| 5,866,713 A | * | 2/1999 | Suzuki et al. ................ 560/205 |
| 5,892,103 A |   | 4/1999 | Sogabe et al. |
| 6,127,586 A | * | 10/2000 | Scott et al. .................. 570/166 |

* cited by examiner

*Primary Examiner*—Robert D. Harlan
(74) *Attorney, Agent, or Firm*—Connolly Bove Lodge & Hutz

(57) ABSTRACT

It is an object of the present invention to provide a process for producing easily polymerizable substance, which can realize stable operation of a purification system, and can stably maintain a production amount by avoiding production stoppage, upon production of an easily polymerizable substance in plural reactors. The present invention is directed to a process for producing easily polymerizable substance, which comprises mixing easily polymerizable substances obtained in plural reactors in advance, and supplying the mixture to a purification apparatus.

12 Claims, 2 Drawing Sheets

PROCESS FOR PRODUCING EASILY POLYMERIZABLE SUBSTANCE

TECHNICAL FIELD

The present invention relates to a process for producing easily polymerizable substance. More particularly, the present invention relates to a process for producing easily polymerizable substance which stably maintains a production amount and is useful for various utilities.

BACKGROUND ART

An easily polymerizable substance is a substance having the polymerizability, which easily causes a polymerization reaction by heat or the like, and is industrially useful as a raw material for forming various compounds or polymers. Among the easily polymerizable substance, as a monomer which is industrially particularly useful, there may be mentioned (meth)acrylic acid. (Meth)acrylic acid is widely used for forming an acrylic fiber copolymer, and an adhesive such as an emulsion and, additionally, is useful also in the field such as paint, fiber procession, leather, construction material and the like, and is indispensable in many chemical fields.

In production of such the easily polymerizable substance, in order to respond to many demands, scale up of a manufacturing facility is required. For example, in production of (meth)acrylic acid, a process by a catalytic gas phase oxidation reaction of propylene or the like has advantage in that an inexpensive manufacturing material can be used, and is industrially advantageous. In this case, since a low boiling point substance, a high boiling point substance and the like are produced as by-products, in addition to (meth)acrylic acid, these by-products and other impurities are separated and removed by a purification system consist of a distillation column and the like, and purified high quality (meth)acrylic acid is supplied.

When an amount of such the easily polymerizable substance such as (meth)acrylic acid and the like to be produced is increased, since there is a limit for one reactor to produce, it is considered to produce the substance in plural reactors. In this case, products obtained in plural reactors are supplied to a purification system and, when products are supplied to a purification system separately, there is a possibility that the easily poylmerizable substance is polymerized in a manufacturing apparatus of a purification system, and manufacturing must be stopped. In such the industrial production, when production is stopped, a production amount can not be stably maintained, this cause troubles in supply of an easily poylmerizable substance such as (meth)acrylic acid and the like which is useful in various fields. Therefore, when the production amount of an easily polymerizable substance is increased, there is room for contrivance to realize stable operation of a purification system and stably supply a purified high quality product.

The prior art cannot be found which describes the technique for realizing stable operation of a purification system, upon obtaining an easily polymerizable substance such as (meth)acrylic acid and the like in plural reactors.

SUMMARY OF THE INVENTION

Accordingly, it is an object of the present invention, which has been made in view of the above-mentioned state of the art, to provide a process for producing easily polymerizable substance, which can realize stable operation of a purification system, and can stably maintain a production amount by avoiding production stoppage, upon production of an easily polymerizable substance in plural reactors.

The present inventors made various investigations concerning a process for supplying an easily polymerizable substance to a purification apparatus to produce a purified easily polymerizable substance, and paid their attention to the fact that, when the substance is produced using plural reactors, a production amount can be maintained in response to many demands, but in this case, a variation is generated in a composition of a solution which is supplied to a purification system from plural reactors. Due to this, an easily polymerizable substance is polymerized in a manufacturing apparatus of a purification system, and there is a possibility that production must be stopped. However, when easily polymerizable substances obtained in plural reactors are mixed in advance and are supplied to a purification apparatus, it becomes possible to realize stable operation of a purification system by reduction in a variation of a composition of a solution supplied to a purification system. Thus, the present inventors found that the above object can be successfully attained.

In addition, the present inventors found that, when mixing of easily polymerizable substances is performed in at least one mixer, or the mixer is a storage tank and a retention time in the storage tank is sufficiently maintained, the effect or the advantage of the present invention is sufficiently exerted and, at the same time, the process for producing an easily polymerizable substance of the present invention is particularly preferable for preparing (meth)acrylic acid, (meth)acrylic acid ester, maleic acid and the like, and a purified high quality product can be supplied while stably maintaining a production amount of a compound useful in various utilities and these findings have now led to completion of the present invention.

That is, the present invention is a process for producing easily polymerizable substance, which comprises mixing easily polymerizable substances obtained in plural reactors in advance, and supplying the mixture to a purification apparatus.

Figure 1:
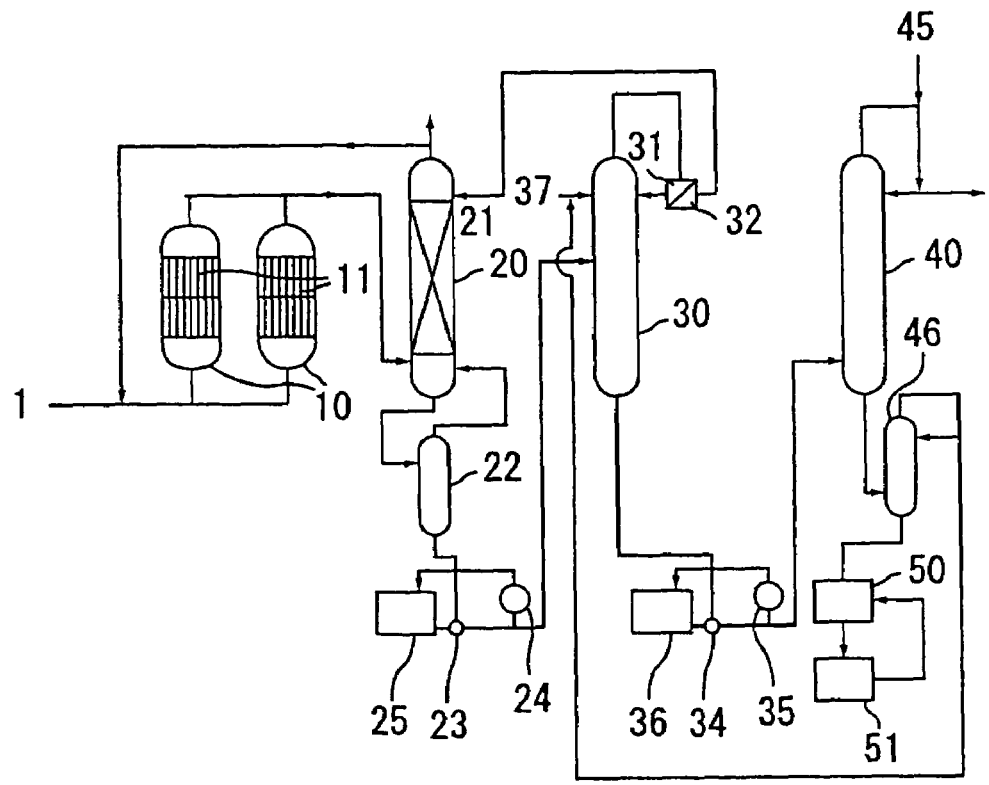
FIG. 1 is a flow-chart showing outline of a process for producing acrylic acid comprising a step of mixing acrylic acid obtained in plural reactors disposed in parallel in advance, and supplying it to a purification apparatus. This is one of preferred embodiments of the present invention.

EXPLANATION OF SYMBOLS 1. raw material gas
2. additional gas
10. catalytic gas phase oxidation reactor (oxidation reactor)
11. catalyst for oxidation reaction
20. capturing column (absorbing column)
21. capturing solvent
22. distillation column
23. pump
24. cooler
25. tank (intermediate tank)
30. azeotropic dehydrating column (water separation column)
31. solvent phase in oil and water separator
32. aqueous phase in oil and water separator
34. pump
35. cooler
36. tank
37. polymerization inhibitor
40. high boiling point substance separation column
45. polymerization inhibitor
46. maleic acid separateion column
50. thin film evaporator
51. thermal decomposition tank
60. esterification reactor
61. tank
70. distillation column
71. oil phase in oil and water separator
72. aqueous phase in oil and water separator
80. acid separation column
81. oil phase
82. aqueous phase
90. alcohol recovery column
100. low boiling point substance separation column
110. purification column
111. purified acrylic ester

DETAILED DESCRIPTION OF THE INVENTION

In the following, the present invention is described in detail.

In the process for producing easily polymerizable substance of the present invention, upon supplying easily polymerizable substances obtained in plural reactors to a purification apparatus, the easily polymerizable substances are mixed in advance. In the present invention, a continuous process is preferable in which a purified easily polymerizable substance is prepared continuously. Easily polymerizable substances obtained in plural reactors, that is, easily polymerizable substances before supply to a purification apparatus are usually a composition containing impurities such as an unreacted substance, by-products and the like together with an easily polymerizable substance, and an easily polymerizable substance obtained after treatment in a purification apparatus contains sufficiently reduced impurities.

As the above-mentioned plural reactors, plural same reactors or plural different reactors may be used. Using plural reactors disposed in parallel is preferred embodiment of the process for producing easily polymerizable substance of the present invention. By using plural reactors, it becomes possible to increase a production amount of an easily polymerizable substance. To obtain easily polymerizable substances in plural reactors means that there are plural reactors for finally producing an easily polymerizable substance. Therefore, when the easily polymerizable substance is finally produced by one reactor, the easily polymerizable substance is produced by plural such the reactors and, when an easily polymerizable substance is finally produced by plural reactors disposed in series, numbers of plural reactors for finally producing an easily polymerizable substances disposed in series are disposed in parallel.

Figure 2:
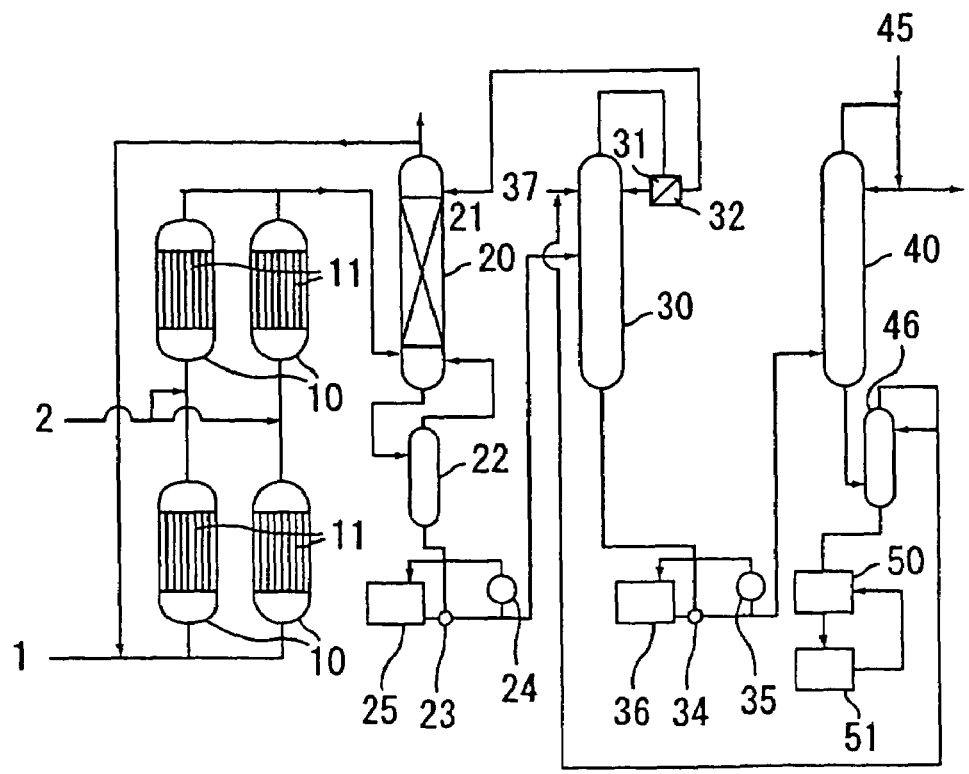
FIG. 2 is a flow-chart showing outline of a process for producing acrylic acid comprising a step of mixing acrylic acid obtained in plural reactors in advance, and supplying it to a purification apparatus. Two sets of reactors disposed in parallel consists of two reactors which are disposed in a former stage and a latter stage in series, and the air, oxygen, water steam or the like can additionally be add to the gas obtained in a former stage reaction if necessary. This is one of preferred embodiments of the present invention.
Figure 3:
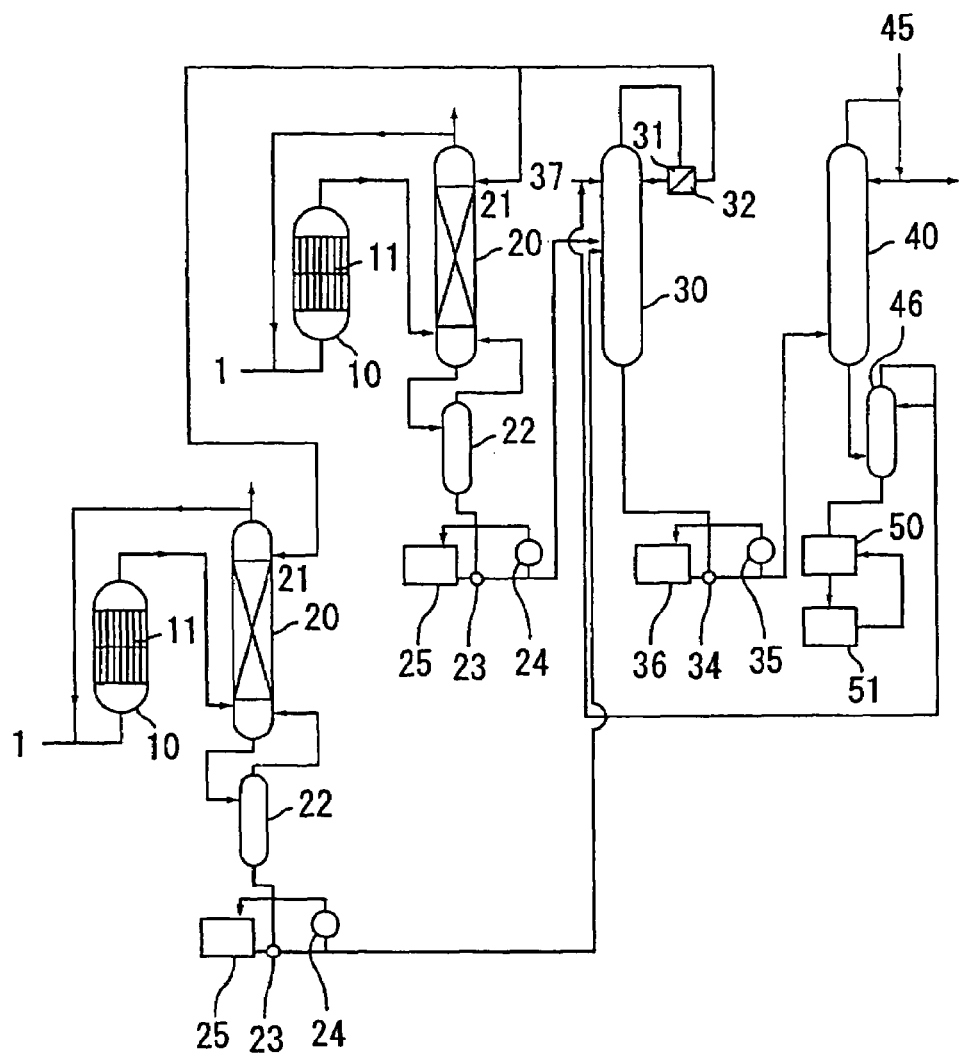
FIG. 3 is a flow-chart showing outline of a process for producing acrylic acid comprising a step of supplying acrylic acids obtained in plural reactors to a water separation column separately.

As the reactor, among oxidation reactors, a shell and tube type (multitubular) heat exchanger is preferable and, in particular, a reactor which is compartmented into plural chambers with an intermediate tube sheet as shown in FIGS. 1 and 3, or a shell and tube type reactor which, if necessary, can further add an air, oxygen, water steam or the like to the gas obtained by the former stage reaction as shown in FIG. 2 are preferable for a two-stage catalytic gaseous oxidation reaction such as the reaction used for producing acrylic acid.

In the present invention, it is enough that a part or all of easily polymerizable substances supplied to a purification apparatus are mixed in advance, and it is preferable that all of the substances are mixed. In addition, it is preferable that all of easily polymerizable substances are mixed, thereby, a difference in compositions due to a difference in reaction products obtained in plural reactors disappears, and a homogeneous easily polymerizable substances-containing solution is obtained.

As a preferable mode of such the process, the above-mentioned mixing of easily polymerizable substances is performed in at least one mixer. When plural mixers are used, plural same mixers or plural different mixers may be used.

As the mixer, it is preferable to use a storage tank, a static mixer, an injector and the like. The storage tank may be a manufacturing facility which can store a liquid substance and, in the present invention, when a column-like manufacturing facility is used, the mixer includes a liquid sump in a column bottom, in addition to a storage tank which is usually used in an industrial manufacturing facility. When the storage tank is used, a mixer may be disposed in the storage tank. When the mixer is disposed, easily polymerizable substances obtained in plural reactors can be mixed by disposing a mixer having a rotating wing or a static mixer. In addition, although mixing may be performed in pipe, it is preferable to dispose a static mixer in order to make mixing effectively and make piping shortest when mixing is performed in pipe.

A static mixer is a mixer having no rotating part, and a line mixer and the like can be used.

When the above-mentioned mixer is used, it is preferable that the mixer is a storage tank, and a retention time in the storage tank is not less than 10 minutes. As a preferable mode in this case, a retention time is not less than 10 minutes without disposing a mixer in a storage tank. Thereby, a variation in a composition of a solution supplied to a purification system becomes much smaller, and it becomes possible to more sufficiently realize stable operation of a purification system which is the effect of the present invention. In addition, it is preferable that the retention time and a mixing method and the like are appropriately set depending on the status of easily polymerizable substance, so that a variation in a composition of a solution supplied to a purification system becomes small. Like this, in the case where easily polymerizable substances obtained in plural reactors are supplied to a purification system, a process of production in which a retention time and a mixing method in a storage tank and the like are appropriately set so that a variation in a composition of a solution supplied to a purification system becomes small, is one of preferred embodiments of the present invention.

In the present invention, purification involves procedures such as distillation, absorption, stripping, extraction, crystallization and the like. In these procedures, as an form of mixing easily polymerizable substances in advance, and supplying mixture to a purification system, easily polymerizable substances may be mixed in a liquid state in advance, and supplied to a purification system, or after easily polymerizable substances may be mixed in the gaseous state, the mixture may be captured in a solvent to convert into a liquid, which may be supplied to a purification system, being not particularly limited. In the present invention, a purification apparatus maybe one or more series and, when the number of reactors and the number of purification system series are different, the effect is more sufficiently exerted.

The present invention is applied to an easily polymerizable substance, which may be polymerized in a purification apparatus. The easily polymerizable substance is a substance having the polymerizability, which easily causes a polymerization reaction by heat, light and the like. For example, a monomer having a radical-polymerizable doublebond is suitable. More preferably, at least one kind selected from the group consisting of (meth)acrylic acid, (meth)acrylic acid ester and maleic acid. The present invention is most preferably applied to acrylic acid which is an easily polymerizable substance having the high necessity of avoiding production stoppage and stably maintaining a production amount.

The process for producing an easily polymerizable substance of the present invention will be explained below, regarding the case that the easily polymerizable substance is acrylic acid, with using the drawings.

In the process of the present invention when acrylic acid is produced, it is preferable to produce acrylic acid by a catalytic gas phase oxidation reaction of a raw material gas such as propylene and the like from a viewpoint that an inexpensive production raw material can be used. In this case, as a raw material gas, it is preferable to use propylene, propane, acrolein or the like as a raw material substance and, in addition to such the raw material substance, gas containing molecular oxygen and an inert gas can be used.

In such the process, a gas having such a composition that the concentration of a raw material substance is not smaller than 1% by volume and not larger than 15% by volume, molecular oxygen is not less than 1-fold and not more than 3-fold of the raw material, and the rest part is an inert gas such as carbon dioxide, water steam and the like, can be used.

FIG. 1 conceptionally shows an industrial facility when acrylic acid is produced as described above, in the process for producing easily polymerizable substance of the present invention.

In FIG. 1, a raw material gas 1 is introduced into two catalytic gas phase oxidation reactors 10 which are disposed in parallel, and a gas containing acrylic acid is produced by reactors 10. The gas, which is produced in this manner, is supplied to a capturing column 20, and captured in water to obtain a solution. In this case, although compositions of gases produced by two reactors 10 are varied, gases are mixed in the capturing column 20, and a variation in a composition becomes small. In addition, a liquid sump at a column bottom of the capturing column 20 is a storage column, which is one of the mixers in the present invention.

Then, the solution is supplied to a distillation column 22 as necessary to remove unnecessary low boiling point substances, a column bottom liquid at a distillation column 22 is transferred to a cooler 24 and a tank 25 by a pump 23, and is supplied to an azeotropic dehydrating column 30 which is one of purification apparatuses. Thereby, a variation in a composition of a solution containing acrylic acid, which is supplied to an azeotropic dehydrating column 30 becomes small, and the effect of the present invention is sufficiently exerted.

In addition, by cooling with a cooler 24, it becomes possible to suppress a production amount of impurities such as an oligomer.

The above-mentioned tank 25 is an intermediate tank, which is disposed between a capturing column 20 and an azeotropic dehydrating column 30, and corresponds to a storage tank of the present invention. Thereby, a variation in a composition of a solution thereafter can be reduced, and stable operation of a purification system can be more sufficiently realized. Like this, by disposing an intermediate tank, even when a trouble occurs in a purification system, the purified product obtained in the reactor 10 can be stored in an intermediate tank. When a catalytic gas phase oxidation reaction is performed, since stoppage of a reactor seriously influences on the productivity, it is preferable to dispose such the intermediate tank in order to avoid production stoppage.

It is preferable that a retention time in such the intermediate tank is not less than 10 minutes and, when acrylic acid is prepared like this, and it is more preferable that the retention time is not less than 20 minutes, still more preferably not less than 40 minutes. In an azeotropic dehydrating column 30, water is removed from a column bottom liquid of a distillation column 22 supplied from a cooler 24 and a tank 25. Thereupon, it is preferable to supply a polymerization inhibitor. By supplying a polymerization inhibitor, a polymerization reaction in the column can be prevented.

Then, a column bottom liquid of an azeotropic dehydrating column 30 is transferred to a cooler 35 and a tank 36 by a pump 34, and is supplied to a high boiling point substance separation column 40 which is a purification apparatus. Acrylic acid purified there is obtained as a distillate. By cooling a column bottom liquid of an azeotropic dehydrating column 30 by disposing a cooler 35 and a tank 36 between an azeotropic dehydrating column 30 and a high boiling substance separation column 40, it becomes possible to suppress a production amount of impurities such as oligomer and the like, to prevent reduction in a yield of acrylic acid, and to sufficiently avoid production stoppage due to occurrence of a polymerization reaction.

A column bottom liquid at a high boiling point substance separation column 40 containing the above-mentioned acrylic acid oligomer and maleic acid is supplied to a column bottom of a maleic acid separation column 46. A part of acrylic acid obtained as a distillate of a maleic acid separation column 46 is supplied to an azeotropic dehydrating column 30 and, at the same time, an acrylic acid oligomer-containing solution is concentrated by a thin film evaporator 50, and thereafter, is thermally degraded in a thermal decomposition tank 51, whereby, purified acrylic acid is obtained. It is preferable, from a viewpoint of improvement in a yield of acrylic acid, to supply a part of a distillate of a maleic acid separation column 46 to an azeotropic dehydrating column 30. In addition, it is preferable to supply a polymerization inhibitor to a high boiling point substance separation column 40, whereby, a polymerization reaction can be prevented and a yield of acrylic acid can be improved.

FIG. 3 shows the case when acrylic acid is produced by a process which does not correspond to the present invention, and conceptionally shows a production step when substances containing acrylic acid obtained in plural reactors 10 are supplied to a purification apparatus without mixing them in advance.

In FIG. 3, two production steps each combining a reactor 10, a capturing column 20, a distillation column 22, a pump 23, a cooler 24, and a tank 25 explained in FIG. 1 are disposed, gases obtained in two reactors 10 are captured separately, and products obtained by these two steps are supplied to an azeotropic dehydrating column 30 separately. In this case, in an azeotropic dehydrating column 30, a composition of a solution at a solution supplying stage is varied, becomes unstable and stable operation of a purification system can not be realized, and a polymer is produced in a purification apparatus. In the present invention, production of such the polymer can be sufficiently suppressed so that a production amount can be stably maintained by realizing stable operation of a purification system and avoiding production stoppage.

In the present invention, acrylic acid ester can be produced from acrylic acid, and in this case, after a step shown in the above-mentioned FIG. 1, the step shown in the following FIG. 4 can be performed. This is one of preferred embodiment of the present invention.

Figure 4:
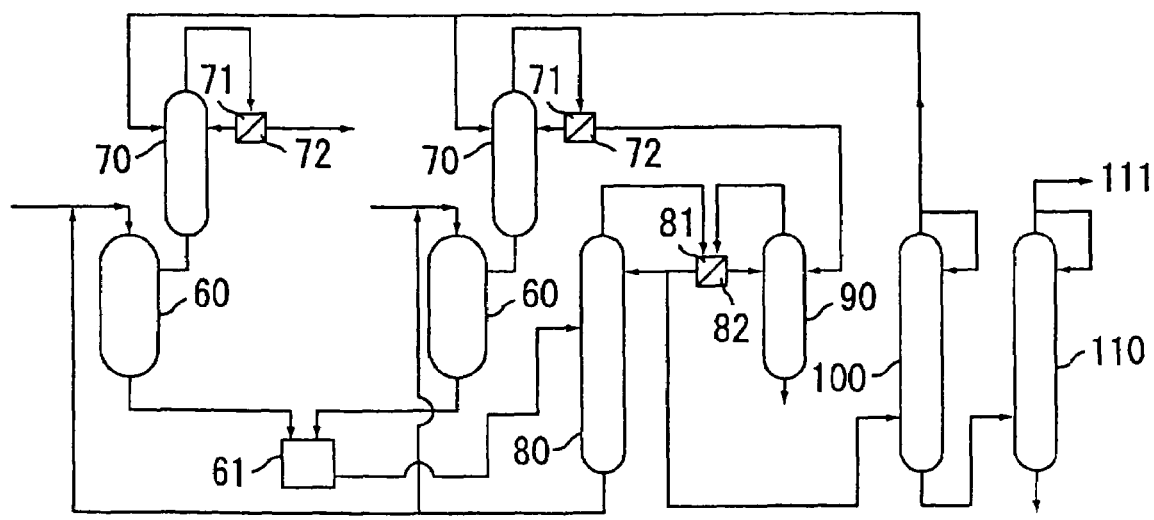
FIG. 4 is a flow-chart showing outline of a process for producing acrylic acid ester from acrylic acid obtained in a step of producing acrylic acid shown in FIG. 1 to FIG. 3.

FIG. 4 conceptionally shows the outline of production step for producing acrylic acid ester from acrylic acid obtained in production step for producing acrylic acid shown in FIG. 1.

In FIG. 4, acrylic acid obtained by a producing step in FIG. 1 is supplied to an esterification reactor 60 together with an alcohol and the like to produce an ester, the ester is retained in a tank 61 for a certain time and, thereafter, a low boiling point substance such as acrylic acid ester, unreacted alcohol, water and the like are removed in an acid separation column 80, then separated into an oil phase 81 containing acrylic acid ester and an aqueous phase 82. The oil phase 81 is supplied to a low boiling point substance separation column 100, and a solution extracted from a column bottom is purified in a purification column 110 to obtain purified acrylic acid ester.

In a process in FIG. 1, it is preferable to use a shell and tube type reactor as a reactor 10 in that it is excellent in a reaction efficiency, and a shell and tube type reactor which is compartmented into plural chambers with an intermediate tube sheet is particularly preferable. For example, when acrolein is used as a raw material substance, a product can be prepared by a one-stage catalytic gas phase oxidation reaction and, when propylene is used as a raw material substance, a product can be prepared by a two-stage catalytic gas phase oxidation reaction.

In the above two-stage catalytic gas phase oxidation reaction, since a reaction rate can be enhanced, it is preferable to perform the reaction in the presence of a catalyst, and a catalyst can be used at a former stage and a latter stage. As the former stage catalyst, for example, a compound represented by the following general formula (1) is preferable.

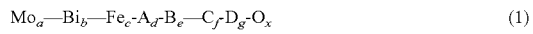

$$Mo_a-Bi_b-Fe_c-A_d-B_e-C_f-D_g-O_x \tag{1}$$

In the above general formula (1), Mo, Bi and Fe represent molybdenum, bismuth and iron, respectively. A represents at least one element selected from nickle (Ni) and cobalt (Co). B represents at least one element selected from an alkali metal and thallium (Tl). C represents at least one element selected from the group consisting of phosphorus (P), niobium (Nb), manganese (Mn), cerium (Ce), tellurium (Te), tungsten (W), antimony (Sb) and lead (Pb). D represents at least one element selected from the group consisting of silicon (Si), alminum (Al), zirconium (Zr), and titanium (Ti). O represents an oxygen atom. Symbols a, b, c, d, e, f, g and x represent an atomic ratio of Mo, Bi, Fe, A, B, C, D and O, respectively. And, when a=12, then b=0.1 to 10, c=0.1 to 10, d=2 to 20, e=0.001 to 5, f=0 to 5, g=0 to 30 and x is a value determined by the oxidation state of each element.

As the above-mentioned latter stage catalyst, a compound represented by the following general formula (2) and the like is preferable.

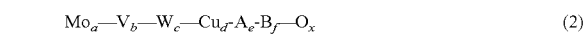

$$Mo_a-V_b-W_c-Cu_d-A_e-B_f-O_x \tag{2}$$

In the above general formula (2), Mo, V, W and Cu represent molybdenum, vanadium, tungsten and copper, respectively. A represents at least one element selected from antimony, bismuth, tin, niobium, cobalt, iron, nickle and chromium (Cr). B represents at least one element selected from an alkali metal, an alkaline earth metal and thallium. C represents at least one element selected from silicon, alminum, zirconium and cerium. O represents an oxygen atom. Symbols a, b, c, d, e, f, g and x represent an atomic ratio of Mo, V, W, Cu, A, B, C and O. And, when a=12, then b=2 to 14, c=0 to 12, d=0.1 to 5, e=0 to 5, f=0 to 5, g=0 to 20, and x is a value determined by the oxidation state of each element.

In the above FIG. 1, acrylic acid is obtained in the gas aqueous state by a catalytic gas phase oxidation reaction, and the acrylic acid-containing gas is supplied to a capturing column 20. In this case, as a capturing method, it is preferable to supply a solvent 21 to the capturing column 20 and capture it with the solvent. As the solvent, it is preferable to use an aqueous solvent having advantages that it is inexpensive and waste water discharged from such the production step can be reused.

When the acrylic acid-containing gas contains unreacted raw material substances, the raw material substances are removed by distillation or stripping and, thereafter, the gas may be supplied to the capturing column 20. In addition, it is preferable to supply the acrylic acid-containing gas to the capturing column 20 after cooling since a capturing efficiency is improved.

As the capturing column 20, a capturing column such as a plate column, a packed column, a wet wall column, a spray column and the like can be used and, usually, it is preferable to use the plate column or the packed column. A packed column is a column in which packing having a large surface area and the permeability is regularly or irregularly packed in the interior thereof. When the packed column is used, an acrylic acid-containing gas is introduced into a capturing column (packed column) 20, a capturing solvent for absorbing acrylic acid introduced into a column from an upper part of the packed column is contacted to the gas in a countercurrent manner on the surface of a packed layer, whereby, acrylic acid is absorbed in a capturing solvent. The capturing condition may be appropriately set depending on a temperature of the gas, an amount of the gas to be supplied per unit time, a volume of the capturing column and the like. For example, it is preferable that a column top temperature of a capturing column is not less than 40° C. and not more than 80° C. When the temperature is less than 40° C., the cooling energy becomes necessary and, additionally, a condense of substance having a low boiling point increases, and this may cause reduction in the purity of the product. When the temperature exceeds 80° C., loss of acrylic acid from a column top of the capturing column increases, and there is a possibility that a product yield is reduced.

A column top pressure in the capturing column 20 is not limited as long as it is a pressure at which a gas can be discharged from a column top, but the pressure is preferably 0 to 30 kPa (gauge pressure). When the pressure is lower than 0 kPa (gauge pressure), an evacuating apparatus becomes necessary and, when the pressure is higher than 30 kPa (gauge pressure), it becomes necessary to scale up a blower for supplying a raw material gas to a catalytic gas phase oxidation reactor. A dilution gas and unreacted raw material components among a gas discharged from a column top can be utilized again in a reaction by circulating them into a reactor 10 in FIG. 1.

Such the condition is preferable that an amount of wetting solution in the above-mentioned capturing column 20 is not less than 0.3 m$^3$/m$^2$·h, more preferably not less than 1 m$^3$/m$^2$·h relative to a column cross-sectional area. When this condition satisfied, since the interior of the capturing column 20 is in the state that assuredly wetted with an appropriate amount of wetting solution, an appropriate amount of liquid can be stored on an gas-liquid contact apparatus, and at the same time, unbalanced stream and stagnation of gas or liquid can be assuredly avoided. In addition, the term "amount of wetting solution" is a value obtained by dividing a solution amount [m$^3$] per unit time supplied to one plate by a column cross-sectional area.

An unreacted reaction raw material, a by-product produced by a reaction and a polymerization inhibitor in addition to acrylic acid are present in a column bottom liquid at a capturing column 20, that is, an acrylic acid-containing aqueous solution, and by circulating this column bottom liquid into a capturing column after cooled by a cooler affiliated to a column bottom part, the acrylic acid concentration in a column bottom liquid can be increased.

When an aqueous capturing solvent is used as the capturing solvent, an aqueous capturing solvent is not limited as long as it can absorb an acrylic acid-containing gas, but the solvent containing water at 80 to 100 parts by mass is preferred. For example, it is preferable that acrylic acid is 0.1 to 5.0% by mass, acetic acid is 0.1 to 10% by mass, and water is 80 to 99.8% by mass. As the capturing solvent, a capturing solvent having the above-mentioned composition adjusted in advance maybe used. For example, an aqueous phase 32 in an oil and water separator affiliated to an azeotropic dehydration column 30 may be used as a solvent for capturing acrylic acid by circulating in a capturing column.

A temperature of the above-mentioned capturing solvent 21 is not limited as long as the solvent can absorb an acrylic acid-containing gas, but since a capturing rate becomes higher, a lower temperature is preferable, and it is preferable that the gas is supplied at a constant temperature in a rage of 0 to 35° C., more preferably 5 to 30° C. In addition, an amount of the solvent is set so that a liquid-gas ratio expressed by a ratio of a solvent amount (L) relative to a supplied gas amount (m$^3$) is preferably 2 to 15 L/m$^3$, more preferably 3 to 12 L/m$^3$, and still more preferably 5 to 10 L/m$^3$. In this step of capturing acrylic acid, it is considered that acrylic acid polymerize, and polymerization of acrylic acid is most easily caused when a ratio by mass of acrylic acid and water is around 50:50. By adopting the ratio of the solvent amount relative to the supplied gas amount in the above-mentioned range, acrylic acid can be effectively captured with preventing polymerization.

In order to prevent polymerization of acrylic acid, it is preferable that the capturing solvent 21 contains a polymerization inhibitor. As a place to supply the polymerization inhibitor-containing solution and the supplying method, the solution may be supplied from any place of the capturing column.

Then, an acrylic acid-containing aqueous solution of the capturing column 20 is supplied to a distillation column 22 as necessary to remove unnecessary low boiling point substances, and a column bottom liquid is transferred by the pump 23 to the cooler 24, where the acrylic acid-containing aqueous solution is cooled. This cooling can reduce a retention time of a high temperature part, and it becomes possible to suppress a production amount of an oligomer. As the cooler, a shell and tube type heat exchanger, a plate type heat exchanger and a spiral type heat exchanger can be used. In the process of FIG. 1, the "low boiling point substance" refers to a substance having a lower boiling point than acrylic acid at a normal state, and the "high boiling point substance" refers to a substance having a higher boiling point than acrylic acid at a normal state.

The acrylic acid-containing aqueous solution is then supplied to the tank 25, and it is preferable that the solution stays in this tank for a certain time. By stay in this tank for a certain time, since an aqueous solution is sufficiently mixed, and a composition becomes uniform, stable operation of purification system becomes possible, and at the same time, production stoppage can be avoided, and it becomes possible to maintain stabilization of a production amount. The column bottom solution of the capturing column 20 may be transferred to the tank 25 without via the distillation column 22, transferred by the pump 23 to the cooler 24, and then, transferred to the next step, and at the same time, a liquid may be circulated in the tank 25. Low boiling point substances, which may be removed in the distillation column 22, can be also removed in the azeotropic dehydration column 30 at a later step, or low boiling point substances may be also separated in other low boiling point substance separation column disposed in other place. That is, an acrylic acid-containing aqueous solution in the process of FIG. 1 broadly comprises acrylic acid containing water before transfer to the azeotropic dehydration column 30 at a later step, such as the column bottom liquid of the capturing column and a column bottom liquid after later distillation. A cooling temperature of the acrylic acid-containing aqueous solution in the tank is preferably not less than 20° C. and not more than 50° C., more preferably not less than 20° C. and not more than 40° C.

Then, the acrylic acid-containing aqueous solution in the tank 25 is supplied to the azeotropic dehydration column 30, and an azeotropic solvent is supplied, followed by azeotropic distillation. As the azeotropic dehydration column 30, a plate column, a packed column, a wet wall column, a spray column and the like can be used. As the azeotropic dehydration column 30, the plate column or the packed column is usually preferable same as the above-mentioned capturing column 20. A preferable theoretical plate number of an azeotropic dehydration column 30 is not less than 3 not more than 30, more preferably not less than 5 and not more than 25.

An amount of the azeotropic solvent to be used is different depending on a content of water contained in an acrylic acid-containing aqueous solution to be supplied to the azeotropic dehydration column 30, and a kind of an azeotropic solvent to be used, and can be used at the previously known rate used in azeotropic utility. From a viewpoint of prevention of polymerization of acrylic acid, a larger amount of an azeotropic solvent is preferable, but as the amount grows larger, a larger amount of the distillation energy becomes necessary.

A temperature of a column top of the above-mentioned azeotropic dehydration column 30 may be appropriately set depending on an amount of water in an acrylic acid-containing aqueous solution to be supplied, an amount of a by-product which is present in admixture therewith, an amount of a liquid to be supplied per unit time, a temperature of a liquid to be supplied, an extent of dehydration of interest, a kind and a content of other components to be separated, a kind of a distillation column which is introduced into a step of purifying acrylic acid and the like, and it is preferable that a column top pressure is 20 to 200 hPa (abs.). A column top temperature is determined by an azeotropic composition which is determined depending on this column top pressure. An oil and water separator is disposed in this azeotropic dehydration column 30, and a distillate from a column top part is introduced into this separator, to separate into a solvent phase 31 in an oil and water separator and an aqueous phase 32 in an oil and water separator, and it is preferable from a viewpoint of efficiency that the oil phase 31 is refluxed into an azeotropic dehydration column 30 at a refluxing ratio of 0.5 to 10, and the aqueous phase 32 is circulated into the capturing column 20, and is used as the capturing solvent 21. Thereby, a column bottom liquid of the azeotropic dehydration column 30 has a composition that a water amount is not more than 0.05% by mass, and the acetic acid concentration is 0.02 to 3% by mass. In the process for producing acrylic acid of FIG. 1, a production efficiency can be further improved by adjusting the concentration of an acrylic acid oligomer (dimer and trimer of acrylic acid) at a column bottom of the azeotropic dehydration column at not more than 5% by weight, preferably not more than 3% by weight.

Here, (abs.) is an absolute pressure.

In the above-mentioned azeotropic dehydration column 30, it is preferable that a polymerization inhibitor is appropriately added in order to prevent polymerization of acrylic acid. Thereupon, when a solution in which the above-mentioned polymerization inhibitor is dissolved in an acrylic acid-containing solution is supplied as a polymerization inhibitor to the azeotropic dehydration column 30, it is suitable in that quality of the product can be improved, and precipitation of a polymerization inhibitor can be prevented.

By azeotropic dehydration treatment by the above-mentioned azeotropic dehydration column 30, water and a low boiling point substance contained in an acrylic acid-containing aqueous solution are removed, and in the process of FIG. 1, a water separation step and a low boiling point substance separation step may be performed separately. Generally, after dehydration treatment, further purification can be performed by a high boiling point substance separation step, and the previously known purification method alone or in combination thereof. A purification method is not limited to a distillation method, but acrylic acid may be purified by crystallization.

After the above-mentioned azeotropic dehydration step and/or low boiling point substance separation step, acrylic acid is preferably cooled by disposing a cooler and/or a tank before the high boiling point substance separation column 40. In the high boiling point substance separation column 40, a step of heating acrylic acid supplied from a tank, and distilling purified acrylic acid out of a column top of a distillation column and, from a viewpoint of thermal efficiency, it is preferable that a temperature of a solution to be supplied is higher. However, since as a temperature of acrylic acid grows higher, an oligomer production rate becomes larger, and a polymerization reaction is easily caused, there is a possibility that a polymer is produced in a high boiling point substance separation column, and a yield of purified acrylic acid is reduced, further, a trouble occurs in continuous operation due to production of a polymer in some cases. On the other hand, when a temperature of acrylic acid is lower than 20° C., a temperature approaches a solidifying point and freezing may be caused, and a large amount of heating becomes necessary at a high boiling point substance removing step. Then, when a solution to be treated is cooled between an azeotropic dehydration treatment and high boiling point substance treatment, it is preferable that a temperature of acrylic acid after cooling is 20 to 50° C. In the process of FIG. 1, when a solution to be treated is cooled between azeotropic dehydration treatment and high boiling point substance treatment, a yield can be improved maximally. As a cooling method, for example, there is a method of transferring a column bottom liquid of the azeotropic dehydration column 30 by the pump 34 to the cooler 35, and storing cooled acrylic acid in the tank 36. In this case, as in the case of transfer to the tank 25, by cooling the solution, a retention time at a high temperature part can be reduced, and it becomes possible to suppress a production amount of an oligomer. As the cooler, a shell and tube type heat exchanger, a plate type heat exchanger, a spiral type heat exchanger and the like can be used.

As the above-mentioned high boiling point substance separation column 40, a plate column, a packed column, a wet wall column, a spray column and the like can be used. As this high boiling point substance separation column, a plate column or a packed column having packing or a plate as an equipment of column inside is preferable, same as in the azeotropic dehydration column 30. A theoretical plate number is preferably 3 to 30, more preferably 5 to 20.

As the distillation condition for the high boiling point substance separation column 40, the previously known distillation condition can be used. For example, distillation can be performed at a column top pressure of 20 to 200 hPa (abs.), and at a column bottom temperature of not more than 120° C.

In addition, in the high boiling point substance separation column 40, it is preferable that a polymerization inhibitor is appropriately added in order to prevent polymerization of acrylic acid as in the above-mentioned azeotropic dehydration column 30.

In the process of FIG. 1, a polymerization inhibitor may be introduced through any part of the column at any distillation column. More preferably, a polymerization inhibitor together with an acrylic acid-containing solution is introduced by spraying through one or more spraying nozzles attached to the distillation column in advance at any part between a raw material supplying plate and a refluxing solution supplying plate, depending on the composition in a high boiling point substance separation column. By spraying, a polymerization inhibitor-containing solution can be scattered over a wide range in the distillation column, and polymerization can be effectively prevented. Also when supplied at a raw material supplying plate and/or a refluxing solution supplying plate, the polymerization inhibitor may be introduced through a spraying nozzle different from a nozzle for a raw material or a refluxing solution, but the raw material, the refluxing solution and the polymerization inhibitor are mixed in advance, and the mixture may be introduced through a spraying nozzle. Thereupon, it is preferable to use a part of a distillate from a column top as acrylic acid. Since the high boiling point substance separation column is an apparatus for obtaining purified acrylic acid, a distillate from a column top has the same quality as that of highly pure acrylic acid which is substantially sufficiently purified and, by using a distillate from this column top, quality of a product is stabilized. A part of an acrylic acid-containing condensed solution obtained by condensing a distilled out gas discharged from a column top part together with a distillate from this column top may be supplied to the azeotropic dehydration column 30.

A column bottom liquid of the above-mentioned high boiling point substance separation column 40 comprises a polymerization inhibitor, acrylic acid oligomer and other high boiling point substances. It is preferable to perform a step of thermally degrading an acrylic acid oligomer comprised in this column bottom liquid to recover acrylic acid.

Thermal decomposition of an acrylic acid oligomer is performed in a thermal decomposition tank 51. A type of the thermal decomposition tank 51 is not particularly limited, but since a column bottom liquid supplied from the high boiling point substance separation column 40 has a high viscosity and, occasionally, precipitation of solid matters is seen and the fluidity is deteriorated, it is preferable that there is a inclination toward a liquid ejection exit and a solution circulating and/or stirring machine is (are) disposed so that a composition in the tank can be uniformized. A thermal decomposition temperature is usually in a range of preferably 120° C. to 220° C., more preferably 120 to 160° C. A retention time (thermal decomposition tank holding solution amount/waste oil amount) is different depending on a thermal decomposition temperature, and usually, around 20 to 50 hours is necessary. For this reason, the thermal decomposition tank 51 requires a heating means, and a decomposition temperature maybe maintained by disposing an jacket to the tank and/or a heat exchanger at inside (or outside) of the tank. In addition, it is better that the concentration of maleic acid contained in a degraded solution obtained by this thermal decomposition is not more than 5% by mass, preferably 0 to 3% by mass, more preferably 0 to 1% by mass.

In order to obtain the above-mentioned degraded solution, it is preferable to dispose a distillation facility such as the maleic acid separation column 46 and the like at an upper part of the decomposition tank 51. A column bottom liquid supplied from the high boiling point substance separation column 40 is supplied to the maleic acid separation column 46, a column bottom liquid obtained from the maleic acid separation column 46 is concentrated in a thin film evaporator 50, and supplied to the thermal decomposition tank 51 to decompose an oligomer. The thin film evaporator 50 is more preferable than shell and tube type heat exchanger in that even a high viscous liquid can be concentrated, and any form of a vertical type and a horizontal type may be used. In the process of FIG. 1, a liquid obtained from the thermal decomposition tank 51 is concentrated again in the thin film evaporator 50 to recover acrylic acid obtained by thermal decomposition. Since acrylic acid is evaporated in the thin film evaporator 50, the acrylic acid may be recovered from a column top part of the maleic acid separation column 46.

As the condition at distillation in the above-mentioned maleic acid separation column 46, a theoretical plate number is preferably 1 to 10, more preferably 1 to 5, and it is preferable that distillation is performed at a column top pressure of 10 to 150 hPa (abs.) and at a column bottom temperature of not more than 120° C.

In addition, in thermal decomposition in the maleic acid separation column 46, the thin film evaporator 50 or the thermal decomposition tank 51, a polymerization inhibitor maybe added. Polymerization can be effectively prevented, and thermal decomposition is promoted in some cases.

It is preferable that acrylic acid recovered by thermally decomposing the above-mentioned oligomer is supplied to a dehydrating step. As described above, by this, impurities such as water and the like which acrylic acid contains in the next step or thereafter can be purified, and a polymerization inhibitor can be effectively utilized. That is, this is suitable in both points of improvement in product quality due to reduction in water in a product and prevention of precipitation of a polymerization inhibitor.

It is preferable that the polymerization inhibitor used in the above capturing column 20, the azeotropic distillation column 30 or the high boiling point substance separation column 40 contains one or more compounds selected from the group consisting of a N-oxyl compound, a phenol compound, a manganese salt such as manganese acetate, dialkyldithiocarbamic acid copper salt such as copper dibutylthiocarbamate, a nitroso compound, and amine compound and phenothiazine. In addition, among a nitroso compound, there are substances which decompose and a component obtained by decomposition exerts the polymerization inhibition effect on acrylic acid, such as N-nitrosophenylhydroxylamine or a salt thereof, for example, an ammonium salt of N-nitrosophenylhydroxylamine, p-nitrosophenol, N-nitrosodiphenylamine and ammonium salts thereof. The polymerization inhibitor in the process of FIG. 1 does not include such substances as a decomposition product of which has the polymerization inhibition effect.

The N-oxyl compound is not particularly limited, but any N-oxyl compounds which are generally known as a polymerization inhibitor for a vinyl compound can be used. Among them, 2,2,6,6-tetramethylpiperidinooxyls represented by the following general formula (3) are suitably used.

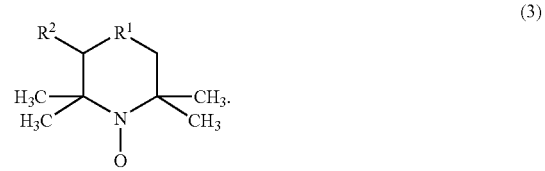

In the general formula (3), $R^1$ represents $CH_2$, CHOH, $CHCH_2OH$, $CHCH_2CH_2OH$, $CHOCH_2OH$, $CHOCH_2CH_2OH$, CHCOOH or C=O. $R^2$ represents a hydrogen atom or $CH_2OH$.

Among the above-mentioned N-oxyl compounds, one or two or more kinds of 2,2,6,6-tetramethylpiperidinoxyl, 4-hydroxy-2,2,6,6-tetramethylpiperidinoxyl and 4,4',4"-tris-(2,2,6,6-tetramethylpiperidinoxyl) phosphite are preferably used. More preferably, 2,2,6,6-tetramethylpiperidinoxyl or 4-hydroxy-2,2,6,6-tetramethylpiperidinoxyl is used. In this case, since a stabilizer type N-oxyl compound is obtained even when a metal is not contained in components, there is no possibility that a metal of a facility is corroded with a stabilizer, and treatment of a waste fluid becomes easy.

As the polymerization inhibitor, in addition to the N-oxyl compound, a N-hydroxy-2,2,6,6-tetramethylpiperidine compound and/or a 2,2,6,6-tetramethylpiperidine compound can be used in combination.

Examples of the N-hydroxy-2,2,6,6-tetramethylpiperidine compound include 1,4-dihydroxy-2,2,6,6-tetramethylpiperidine, 1-hydroxy-2,2,6,6-tetramethylpiperidine and the like. One or two or more kinds of these N-hydroxy-2,2,6,6-tetramethylpiperidine compounds can be used.

Examples of the 2,2,6,6-tetramethylpiperidine compounds include 2,2,6,6-tetramethylpiperidine, 4-hydroxy-2,2,6,6-tetramethylpiperidine and the like, and one or more kinds of these can be used. In addition, a N-hydroxy-2,2,6, 6-tetramethylpiperidine compound or a 2,2,6,6-tetramethylpiperidine compound is contained in commercially available N-oxyl compound products as impurities in some cases. In such the case, use of the commercially available N-oxyl compound results in concomitant use of a N-hydroxy-2,2,6,6-tetramethylpiperidine compound or a 2,2,6,6-tetramethylpiperidine compound.

Examples of the above phenol compound include hydroquinone and methoquinone (p-methoxyphenol). Since the polymerization inhibiting effect when used combining with a N-oxyl compound and a phenothiazine compound is superior over that of hydroquinone, methoquinone is preferable. These phenol compounds can be used alone or in combination of two or more species.

Examples of the above phenothiazine compound include phenothiazine, bis-α-methylbenzyl)phenothiazine, 3,7-dioctylphenothiazine, bis-(α-dimethylbenzyl)phenothiazine and the like.

The above-mentioned copper salt compound is not particularly limited, but any of an inorganic salt and an organic salt may be used. Examples thereof include copper dialkyldithiocarbamate, copper acetate, copper naphthenate, copper acrylate, copper sulfate, copper nitrate, copper chloride and the like. Any of monovalent and divalent these copper salt compounds may be used. Among the above-mentioned copper salt compounds, copper dialkyldithiocarbamate is preferable from a viewpoint of the effect etc.

Examples of the copper dialkyldithiocarbamate include copper dimethyldithiocarbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyldithiocarbamate, copper methylpentyldithiocarbamate, copper methylhexyldithiocarbamate, copper methylphenyldithiocarbamate, copper ethylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithiocarbamate, copper butylpentyldithiocarbamate, copper butylhexyldithiocarbamate, copper butylphenyldithiocarbamate, copper pentylhexyldithiocarbamate, copper pentylphenyldithiocarbamate, copper hexylphenyldithiocarbamate and the like. These copper dialkyldithiocarbamates may be a monovalent copper salt or a divalent copper salt. Among them, from a viewpoint of the effect and easy availability, copper dimethyldithiocarbamate, copper diethyldithiocarbamate and copper dibutyldithiocarbamate are preferable, and copper dibutyldithiocarbamate is more preferable.

Examples of the above manganese salt compound include manganase dialkyldithiocarbamate, manganese diphenyldithiocarbamate, manganese formate, manganese acetate, manganese octanoate, manganese naphthenate, manganese permanganate, a manganese salt compound of ethylenediaminetetraacetic acid and the like having a same or different alkyl group selected from methyl, ethyl, propyl, and butyl. These may be used alone or in combination of two or more species.

An amount of the polymerization inhibitor is appropriately adjusted depending on the operation condition, being not particularly limited. It is preferable that a total amount of a polymerization inhibitor used is 3 to 3500 ppm (based on mass) relative to a mass of acrylic acid in a captured reaction gas. A preferable amount of individual polymerization inhibitor is such that the amount of the N-oxyl compound is 1 to 500 ppm relative to a mass of acrylic acid in a reaction gas, the amount of the manganese salt compound or the copper salt compound is 1 to 200 ppm relative to a mass of acrylic acid in a reaction gas, the amount of the nitroso compound is 1 to 500 ppm, the amount of the phenol compound is 1 to 500 ppm, the amount of the phenothiazine compound is 1 to 500 ppm, the amount of the N-hydroxy-2,2,6,6-tetramethylpiperidine compound is 1 to 500 ppm, and the amount of the 2,2,6,6-tetramethylpiperidine compound is 1 to 500 ppm.

It is preferable that the polymerization inhibitor is dissolved in a solvent, and supplied as a polymerization inhibitor-containing solution. When supplied as a polymerization inhibitor-containing solution, since a polymerization inhibitor is uniformly dispersed in the column, this has advantage that the polymerization inhibiting effect becomes high. As a solvent for dissolving a polymerization inhibitor, an acrylic acid-containing solution is preferable. When a polymerizaiton inhibitor is supplied together with acrylic acid, since water and a solvent are evaporated, but acrylic acid is not evaporated and is transferred to a column bottom side at a place above an acrylic acid-containing gas supplying stage of the capturing column 20 when supplied to, for example, the capturing column 20, if acrylic acid is present, it is advantageous in that a polymerization inhibitor is accompanied with acrylic acid, and precipitation of a polymerization inhibitor can be prevented. When a thermal decomposition product of an acrylic acid oligomer is used as acrylic acid, acrylic acid is effectively utilized, and the productivity can be improved. For example, when the acrylic acid is contained in the capturing solvent 21, the capturing solvent 21, or a part of acrylic acid obtained in other step, or a solution after the acrylic acid oligomer described later is thermally decomposed, or a column bottom liquid of a capturing column can be used as an acrylic acid-containing solution. It is preferable that, in the capturing column 20, in particular, a waste solution from steam ejector used in a step of producing acrylic acid is used as an acrylic acid-containing solution. A waste solution from a steam ejector is an aqueous solution containing acrylic acid, and since a composition ratio thereof is not considerably different from the solution composition in a capturing column, thereby, reduction in the absorption efficiency in a capturing column can be prevented. When the acrylic acid concentration in an acrylic acid-containing solution used is higher than an acrylic acid composition in a capturing column, reduction in the absorption efficiency or polymerization may be caused. In such the process, an oligomer refers to a Michael-type adduct of acrylic acid represented by the following general formula (4).

$$R\text{—}COO\text{—}(X\text{—}COO)_n\text{—}H \tag{4}$$

In the general formula (4), —X— represents —CH$_2$CH$_2$— or —CH(CH$_3$)—, n represents an integer of 1 to 5, provided that when n is 2 or more, plural-X-s may be the same or different.

In addition, as a polymerization inhibitor having the thermal decomposition promoting activity used in the maleic acid separation column 46, the thin film evaporator 50 or the thermal decomposition tank 51, among polymerization inhibitors which can be used in the above-mentioned capturing column 20, one or more kinds of 4,4',4"-tris-(2,2,6,6-tetramethylpiperidinooxyl) phosphite and 2,2,6,6-tetramethylpiperidinooxyls represented by the following general formula (3):

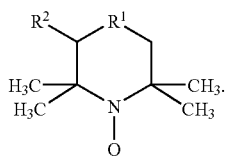
(3)

(In the above general formula (3), $R^1$ represents $CH_2$, CHOH, $CHCH_2OH$, $CHCH_2CH_2OH$, $CHOCH_2OH$, $CHOCH_2CH_2OH$, CHCOOH or C=O, and $R^2$ represents a hydrogen atom or $CH_2OH$), and one or more of N-hydroxy-2,2,6,6-tetramethylpiperidine compound such as 1,4-dihydroxy-2,2,6,6-tetramethylpiperidine, 1-hydroxy-2,2,6,6-tetramethylpiperidine and the like, and 2,2,6,6-tetramethylpiperidine compound such as 2,2,6,6-tetramethylpiperidine, 4-hydroxy-2,2,6,6-tetramethylpiperidine and the like can be used in combination.

Examples of an azeotropic solvent used in the azeotropic dehydration column 30 include a solvent containing at least one kind selected from heptane, dimethylcyclohexane, ethylcyclohexane, toluene, ethylbenzene, chlorobenzene, xylene and a mixture thereof; a solvent containing at least one kind selected from diethyl ketone, diisopropyl ketone, methyl propyl ketone, methyl isobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acrylate, isopropenyl acetate, vinyl propionate, propyl propionate, methyl crotonate, methyl valerate, ethyl butyrate, dibutyl ether and a mixture thereof; and a mixed solvent of a solvent containing at least one kind selected from heptane, dimethylcyclohexane, ethylcyclohexane, toluene, ethylbenzene, chlorobenzene, xylene and a mixture thereof, and a solvent containing at least one kind selected from diethyl ketone, diisopropyl ketone, methyl propyl ketone, methyl isobutyl ketone, methyl t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl butyrate, dibutyl ether and a mixture thereof.

As an azeotropic solvent used in the azeotropic dehydration column 30, among the above-exemplified compound, a solvent containing at least one kind selected from heptane, toluene and a mixture thereof; a solvent containing at least one kind selected from ethyl methacrylate, methyl isobutyl ketone, n-propyl acrylate, n-butyl acetate and a mixture thereof; a mixed solvent of a solvent containing at least one kind selected from heptane, toluene and a mixture thereof, and a solvent containing at least one kind selected from ethylmethacrylate, methyl isobutyl ketone, n-propyl acrylate, n-butyl acetate and a mixture thereof; are preferable.

In the process for producing acrylic acid ester in FIG. 4, purified acrylic acid obtained in the high boiling point substance separation column 40 in FIG. 1 is supplied to an esterification reactor 60 charged with a strong acid cationic exchanging resin as a catalyst, and an alcohol and others are introduced therein to perform an esterification reaction. Then, a reaction solution containing produced acrylic acid ester is transferred to a tank 61, and the solution stays there for a certain time. Thereby, a difference in compositions of reaction products due to reactors is homogenized, a variation of a liquid composition of the reaction solution containing acrylic acid ester supplied to an acid separation column 80 is reduced, and it becomes possible to obtain the same action and the effect as that of the above-mentioned step of preparing acrylic acid. A retention time in the tank is preferably 20 minutes or longer, more preferably 40 minutes or longer. Then, the reaction solution of the tank is introduced into the acid separation column 80. Low boiling point substances such as acrylic acid ester, unreacted alcohol, water and the like are distilled out of a column top, thereafter the distillate from a column top of the acid separation column 80 is introduced into an oil and water separator, and is separated into an oil phase 81 containing acrylic acid ester and an aqueous phase 82 containing water and alcohol as main components. The aqueous phase 82 together with an aqueous phase 72 in the oil and water separator of the column top distillate of a water separation column 70 is transferred to an alcohol recovery column 90, and the oil phase 81 is supplied to a low boiling point substance separation column 100. Thereupon, a part of the oil phase 81 may be refluxed to the acid separation column 80. Acrylic acid ester discharged from a column bottom of the low boiling point separation column 100 is supplied to a purification column 110, and acrylic acid ester 111 purified from the column top is distilled out. In addition, an alcohol distilled from a column top of the alcohol recovery column 90 may be supplied to the oil phase 81 in the oil and water separator affiliated to the acid separation column 80. Furthermore, water, alcohol and other low boiling point substance distilled from the column top of the low boiling point substance separation column 100 are circulated into the esterification reactor 60 via a distillation column 70 equipped at an upper part of the esterification reactor 60.

In the above-mentioned process for producing acrylic acid ester, a column bottom liquid of the acid separation column 80 contains a raw material component such as acrylic acid and the like, an acrylic acid dimer and an ester of an acrylic acid dimer, and a Michael-type adduct represented by the following general formula (5) such as alcoxypropionic acid and alcoxypropionic acid ester. For this reason, the column bottom liquid of the acid separation column 80 may be supplied to the esterification reactor 60 as shown in FIG. 4, or may be supplied to the separately disposed thin film evaporator and decomposition tank to degrade an acrylic acid oligomer. Thereby, components contained in the column bottom liquid are degraded and, by introduction of the thin film evaporator, alcohol, acrylic acid and acrylic acid ester are obtained, and these are introduced again into the esterification reactor 60, whereby, it becomes possible to improve a yield of acrylic acid ester. In addition, also in decomposition of the column bottom liquid, the decomposition reaction can be promoted by adding the above-mentioned N-oxyl compound or the like.

(5)

In the above-mentioned general formula, m represents an integer of 1 to 5. $R^1$ and $R^2$ may be the same or different, and each represents a hydrogen atom or an alkyl group. —X— represents —$CH_2$—$CH_2$— or —$CH(CH_3)$— with a proviso that, when m is 2 or larger, plural (—X—)s may be the same or different.

The above-mentioned process for producing acrylic acid ester is a method of obtaining an ester by a dehydration reaction of acrylic acid and alcohol, and examples of a preferable alcohol include various alcohols such as methanol, ethanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, lauryl alcohol and the like. These may be straight or branched. In addition, these may be used alone or in combination of two or more. Furthermore, the reaction condition, the distillation condition and the like of the above-mentioned respective steps, the previously known conditions can be adopted.

On the other hand, purified acrylic acid obtained from a high boiling point substance separation column 40 in FIG. 1 can be distilled or crystallized to obtain highly pure acrylic acid. In the case of distillation, a method can be used that comprise steps of adding the known primary amine and/or salt thereof such as hydrazine hydrate, phenylhydrazine and the like together with purified acrylic acid to a distillation column at 1.0 to 10.0 mol, more preferably 1.0 to 5.0 mol relative to 1 mol of contained aldehyde and, after addition of a treating agent, and performing distillation under reduced pressure in a distillation column such as a flash column equipped with a mist separator under the conditions of a column top (distillation column-top) pressure of 10 to 150 hPa (abs.), and a column top temperature of 35 to 90° C. By this treatment, highly pure acrylic acid can be obtained which has a content of aldehydes such as furfural, acrolein, benzaldehyde and the like of 10 ppm by mass or smaller. Alternatively, equivalent highly pure acrylic acid maybe obtained by crystallization using a crystallization device. When a water-absorbing resin is prepared from acrylic acid, since odor or stimulation on a skin due to the impurities contained in above-mentioned acrylic acid is not preferable in some cases depending on utilities, it is preferable to use such the highly pure acrylic acid.

Since the process for producing an easily polymerizable substance of the present invention has the above-mentioned essential features, upon preparation of an easily polymerizable substance by plural reactors, stable operation of a purification system can be realized, and stoppage of preparation can be avoided to stably maintain a production amount, therefore, there can be provided a process for producing an easily polymerizable substance which is industrially useful as a manufacturing raw material for forming various compounds and polymers.

BEST MODE FOR CARRYING OUT THE INVENTION

The present invention will be explained in more detail by way of Examples, but the present invention is not limited to these Examples. Unless otherwise indicated, "part" means "part by weight", "wt %" means "% by mass", and "vol %" means "% by volume".

EXAMPLE 1

According to a flow shown in FIG. 1, acrylic acid was prepared. First, propylene was catalytic gaseous phase-oxidized with a molecular oxygen gas in a shell and tube type reactor which is compartmented into plural chambers with an intermediate tube sheet, in the presence of an oxidation catalyst, to obtain a mixed gas containing 7.1 vol % of acrylic acid, 0.3 vol % of acetic acid, and 14.7 vol % of water. This gas was introduced into an absorbing column (capturing column) (Cascade Mining 3P 10 m) to obtain a column bottom liquid. This absorbing column was operated at a pressure at a column top part of 1100 hPa abs. and a temperature of 62° C., and water containing 1.5 wt % of acrylic acid and 5.4 wt % of acetic acid obtained by mixing a part of separated water produced from an azeotropic dehydration column and waste water produced from a distillation column vacuum-generating apparatus, and water was supplied as capturing water from the column top together with hydroquinone as a polymerization inhibitor. In addition, a part of a discharged gas of the column top was circulated into an oxidation reactor (catalytic gaseous oxidation reactor), and the reminder was discharged as a waste gas to the outside of the system. A column bottom liquid of the absorbing column was further distilled to obtain an aqueous acrylic acid solution containing 70 wt % of acrylic acid, 3.4 wt % of acetic acid and 0.3 wt % of maleic acid.

The resulting aqueous acrylic acid solution was cooled to 40° C. through a cooler affiliated to a tank disposed between a water separation column (azeotropic dehydration column) (retention time in column and tank; 2 hours), and the aqueous solution together with a part of a distillate of a maleic acid separation column was supplied to an intermediate plate of a water separation column equipped with a 50-stages perforated tray without downcomer. In the water separation column, azeotropic separation operation was performed using toluene at a pressure of a column top of 190 hPa (abs.) and a refluxing ratio of 1.0 (total mol number of refluxing liquid per unit time/total mol number of distillate per unit time). A distillate of the water separation column together with water of a steam ejector, which is a vacuum-generating apparatus, was guided to a storage tank, and separated into an organic phase and an aqueous phase. Copper dibutyldithiocarbamate salt and hydroquinone monomethyl ether as a polymerization inhibitor for the column were dissolved in a refluxing liquid in advance, and mixed with the refluxing liquid. Separately, hydroquinone dissolved in water together with a part of a distillate of the maleic acid separation column was placed by spraying between an acrylic acid aqueous solution supplying stage and a refluxing liquid supplying step. A column bottom liquid was further cooled to 40° C. through a cooler affiliated to a tank disposed between a high boiling separation column (high boiling point substance separation column), and supplied to an intermediate plate of the high boiling separation column equipped with a 45-stages perforated tray without downcomer. The column was operated at a column top pressure of 45 hPa (abs.) and a refluxing ratio of 1.4. Acrylic acid was obtained from the column top. A column bottom liquid of the column contains 31 wt % of acrylic acid oligomer and 5 wt % of maleic acid, and was supplied to a column bottom of the maleic acid separation column equipped with a 5-stages perforated tray without downcomer. The column was provided with a thin film evaporator and a thermal decomposition tank at the column bottom thereof, and was operated at 45 hPa (abs.) and a refluxing ratio of 0.5, to obtain acrylic acid containing 0.5 wt % of maleic acid from the column top. On the other hand, bottom liquid from the thin film evaporator was introduced into the thermal decomposition tank, and thermally degraded at a temperature of 150° C. for a retention time of 40 hours, a part of bottom liquid were circulated into the thin film evaporator. Copper dibutyldithiocarbamate salt and hydroquinone monomethyl ether as a polymerization inhibitor were dissolved in acrylic acid, which was introduced by spraying into a condenser in the high boiling separation column and the maleic acid separation column. A waste fluid was discarded from the thermal decomposition tank at a composition of 5.5 wt % of acrylic acid and 39 wt % of acrylic acid oligomer. After stable operation for about 3 months, the apparatus was stopped, the interior of the apparatus was checked, and no problem was found.

EXAMPLE 2

According to the same manner as that of Example 1 except that the tank before supply to the water separation column was not used (retention time in column; 30 min.) in Example 1, the same operation was performed. After stable operation for about 3 months, the apparatus was stopped, the interior thereof was checked, and no problem was found.

EXAMPLE 3

According to the same manner as that of Example 1 except that the tank before supply to the water separation column was not used (retention time in column; 8 min.) in Example 1, the same operation was performed. Slight disturbance was seen in a temperature in the water separation column was seen and, after operation for about 3 months, the apparatus was stopped, the interior thereof was checked, and a small amount of a polymer was confirmed in the column.

COMPARATIVE EXAMPLE 2

According to a flow shown in FIG. 3, acrylic acid was prepared. According to the same manner as that of Example 1 except that a retention time in a column and tank was 2 hours, and aqueous acrylic acid solutions obtained in a shell and tube type reactor which is compartmented into plural chambers with an intermediate tube sheet were supplied to the water separation column separately, the same operation was performed. Disturbance was seen in a temperature in the water separation column. After operation for about 1 month, the apparatus was stopped, the interior thereof was checked, and a polymer was confirmed in the column.

EXAMPLE 4

According to a flow shown in FIG. 4, butyl acrylate was prepared. A reaction of esterifying acrylic acid and n-butanol was performed in a cylindrical-type reactor while stirring a reaction solution. As a catalyst for the reaction, a strong acid cationic exchanging resin (manufactured by Mitsubishi Chemical Co., Ltd.; trade name "Diaion PK208") was used, and the reaction was performed under the reaction condition of a temperature of 80° C. and a pressure of 20 kPa (absolute pressure) The resulting reaction solution was supplied to an acid separation column via a tank (retention time in tank; 30 min.), and a product was obtained via a purification step successively. After stable operation of about 4 months, the apparatus was stopped, the interior thereof was checked, and no problem was seen.

COMPARATIVE EXAMPLE 3

The same operation as that of Example 4 was performed except that the reaction solution was separately and directly supplied to the acid separation column without via the storage tank. After stable operation for about 4 months, the apparatus was stopped, the interior thereof was checked, and a small amount of a polymer was confirmed.

The present application claims priority under 35 U.S.C. §119 to Japanese Patent Application No.2003-136374, filed May 14, 2003, entitled "PROCESS FOR PRODUCING EASILY POLYMERIZABLE SUBSTANCE"

The contents of that application are incorporated herein by reference in its entirety.

The invention claimed is:

1. A process for producing easily polymerizable substance, which comprises mixing, in advance, easily polymerizable substances obtained in plural reactors disposed in parallel thereby preparing a mixture, and supplying the mixture to a purification apparatus, wherein a same reaction is carried out in the plural reactors, and wherein the easily polymerizable substance is at least one kind selected from the group consisting of (meth)acrylic acid, (meth)acrylic acid ester and maleic acid, and wherein the mixing of easily polymerizable substance is performed in at least one mixer.

2. The process for producing easily polymerizable substance according to claim 1 wherein the mixer is a storage tank, and a retention time in the storage tank is not less than 10 minutes.

3. The process for producing easily polymerizable substance according to claim 1, wherein the purification apparatus is the apparatus for distillation, absorption, striping, extraction, crystallization, acid separation or capturing.

4. The process for producing easily polymerizable substance according to claim 1, wherein the easily polymerizable substance is mixed in a gaseous state or a liquid state in advance.

5. The process for producing easily polymerizable substance according to claim 1, wherein the mixer is a liquid sump at a column bottom.

6. The process for producing easily polymerizable substance according to claim 1, wherein an intermediate tank is used as a storage tank.

7. The process for producing easily polymerizable substance according to claim 1, wherein the reactor is a shell and tube catalytic gas phase reactor.

8. The process for producing easily polymerizable substance according to claim 1, wherein the easily polymerizable substance is (meth)acrylic acid or maleic acid.

9. The process for producing easily polymerizable substance according to claim 1, wherein the easily polymerizable substance is (meth)acrylic acid and a liquid sump at a column bottom of a capturing column is used as a storage tank.

10. The process for producing easily polymerizable substance according to claim 6, wherein the intermediate tank is disposed between a capturing column and a azeotropic dehydration column.

11. The process for producing easily polymerizable substance according to claim 1, wherein the reactor is an esterification reactor and the easily polymerizable substance is a (meth)acrylic acid ester.

12. The process for producing easily polymerizable substance according to claim 11, wherein a tank used as a storage tank is disposed between the esterification reactor and an acid separation column.

* * * * *